US 12,398,090 B2

United States Patent
Joedecke et al.

(10) Patent No.: US 12,398,090 B2
(45) Date of Patent: Aug. 26, 2025

(54) SEPARATION OF N-METHYLETHYLENEDIAMINE FROM EDA-CONTAINING MIXTURES

(71) Applicant: BASF SE, Ludwigshafen am Rhein (DE)

(72) Inventors: Michael Joedecke, Ludwigshafen am Rhein (DE); Joerg Pastre, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 700 days.

(21) Appl. No.: 17/783,280

(22) PCT Filed: Dec. 3, 2020

(86) PCT No.: PCT/EP2020/084404
§ 371 (c)(1),
(2) Date: Jun. 8, 2022

(87) PCT Pub. No.: WO2021/115907
PCT Pub. Date: Jun. 17, 2021

(65) Prior Publication Data
US 2023/0008827 A1    Jan. 12, 2023

(30) Foreign Application Priority Data

Dec. 13, 2019 (EP) .................................... 19216120

(51) Int. Cl.
*C07C 67/48* (2006.01)
*C07C 29/141* (2006.01)
(Continued)

(52) U.S. Cl.
CPC ............ *C07C 67/48* (2013.01); *C07C 29/141* (2013.01); *C07C 209/84* (2013.01); *C07C 209/86* (2013.01); *C07C 211/10* (2013.01)

(58) Field of Classification Search
None
See application file for complete search history.

(56) References Cited

U.S. PATENT DOCUMENTS

| 2,519,803 A | 8/1950 | George et al. |
| 2,861,995 A | 11/1958 | Mackenzie |

(Continued)

FOREIGN PATENT DOCUMENTS

| CN | 102190588 A | 9/2011 |
| CN | 102233272 A | 11/2011 |

(Continued)

OTHER PUBLICATIONS

International Search Report and Written Opinion received for PCT Patent Application No. PCT/EP2020/084404, mailed on Feb. 18, 2021, 7 pages.

(Continued)

*Primary Examiner* — Renee Claytor
*Assistant Examiner* — Jennifer C Sawyer
(74) *Attorney, Agent, or Firm* — Faegre Drinker Biddle & Reath LLP (57) ABSTRACT

A process for producing EDA from a mixture comprising water (H2O), ethylenediamine (EDA) and N-methylethylenediamine (NMEDA) by feeding the mixture into a rectification column, wherein the rectification column is operated at the top pressure in the range of 5.0 to 7.5 bar.

15 Claims, 2 Drawing Sheets

(51) Int. Cl.
   *C07C 209/84* (2006.01)
   *C07C 209/86* (2006.01)
   *C07C 211/10* (2006.01)

(56) References Cited

U.S. PATENT DOCUMENTS

| | | | |
|---|---|---|---|
| 3,112,318 A | 11/1963 | Lemon et al. | |
| 3,137,730 A | 6/1964 | Fitz-William | |
| 4,111,840 A | 9/1978 | Best | |
| 2017/0217874 A1 | 8/2017 | Luyken et al. | |
| 2020/0308098 A1* | 10/2020 | Luyken | C07C 209/84 |

FOREIGN PATENT DOCUMENTS

| | | |
|---|---|---|
| DE | 1154121 B | 9/1963 |
| DE | 1172268 B | 6/1964 |
| DE | 1258413 B | 1/1968 |
| EP | 2346809 A1 | 7/2011 |
| EP | 2487151 A1 | 8/2012 |
| EP | 2507202 A1 | 10/2012 |
| JP | 2017-513924 A | 6/2017 |
| WO | 2007/093514 A1 | 8/2007 |
| WO | 2008/104552 A1 | 9/2008 |
| WO | 2008/104582 A2 | 9/2008 |
| WO | 2008/104592 A1 | 9/2008 |
| WO | 2019/081284 A1 | 5/2019 |

OTHER PUBLICATIONS

European Search Report for EP Patent Application No. 19216120.6, Issued on Jun. 9, 2020, 3 pages.

Fulgueras, et al., "Optimization study of pressure-swing distillation for the separation process of a maximum-boiling azeotropic system of water-ethylenediamine", Korean Journal of Chemical Engineering, vol. 33, Issue 1, Sep. 14, 2015, pp. 46-56.

International Preliminary Report on Patentability received for PCT Patent Application No. PCT/EP2020/084404, mailed on Mar. 28, 2022, 6 pages.

Michael Arne, "Chapter: 6 Ethyleneamines From Monoethanolamine", Alkyl Amines, Sri International, Mar. 1981, 25 pages.

Roose, et al., "Chapter 8 : Diamines and Polyamines", Amines, Aliphatic, Ullmann's Encyclopedia of Industrial Chemistry, Sep. 30, 2015, pp. 35-41.

* cited by examiner

SEPARATION OF N-METHYLETHYLENEDIAMINE FROM EDA-CONTAINING MIXTURES

This application is a national stage application (under 35 U.S.C. § 371) of PCT/EP2020/084404, filed Dec. 3, 2020, which claims benefit of European Application No. 19216120.6, filed Dec. 13, 2019, both of which are incorporated herein by reference in their entirety.

DESCRIPTION

The present invention relates to a process for separating N-methylenediamine from EDA-containing mixtures.

Ethylenediamine is used predominantly as an intermediate for the production of bleach activators, crop protection agents, pharmaceuticals, lubricants, textile resins, polyamides, paper auxiliaries, gasoline additives and many other substances.

There are numerous known processes for preparing EDA (see, for example, Ullmann's Encyclopedia of Industrial Chemistry, "Amines Aliphatic", section 8.1.1. DOI: 10.1002/1436007.a02_001).

In the preparation of ethylenediamine, N-methylethylenediamine (NMEDA) can be formed by side reactions.

For example, in the reaction of monoethanolamine (MEA) with ammonia to give EDA, a degradation reaction of monoethanolamine can directly give rise to carbon monoxide (CO) and methylamine (decarbonylation). The methylamine can in turn react directly with further monoethanolamine to give NMEDA.

NMEDA can also form in the dimerization of monoethanolamine to aminoethanolamine (AEEA) when AEEA is degraded directly by decarbonylation to NMEDA.

NMEDA can also form in the preparation of EDA from C1 units such as hydrogen cyanide and formaldehyde.

As well as NMEDA, poly-N-methylated ethylenediamines can also form, for example bis(N-methyl-1,2-ethanediamine). In terms of amount, however, the formation of NMEDA is typically dominant.

For most industrial applications, the market demands a purity for EDA of at least 99.5% by weight. Organic secondary components, including NMEDA, may be present with a proportion of not more than 0.5% by weight. Furthermore, the water content may be not more than 0.5% by weight.

More particularly, in many industrial applications, a purity of EDA is specified where the proportion of NMEDA is below 1000 ppm by weight.

EDA which, as a result of its preparation, has a higher NMEDA content has to be worked up correspondingly, so as to obtain EDA that has the required specifications.

In a mixture comprising EDA, water and NMEDA, the NMEDA is usually separated from EDA and water under azeotropic conditions.

EP2487151 (DOW) presents a process for depleting alkylethyleneamines from ethyleneamine mixtures, wherein a mixture consisting of ethylenediamine, water and one or more alkylethylenediamines is subjected to such conditions that an azeotrope is formed between the water and the alkylethyleneamines, which is separated from the remaining composition. It is disclosed that the pressure in the rectification column in which the azeotrope of water and alkylethylenediamine is separated off is in the range from 1.01 to 2.12 bar, preferably 1.5 to 1.98 bar. In example 1, the distillation is effected at a top pressure of 1.634 bar, a top temperature of 115° C. and a bottom temperature of 176° C.

Apart from these technical details relating to the distillation, the disclosure does not contain any further technical information as to which measures the person skilled in the art has to take in order that an azeotrope of alkylethyleneamine and water is formed.

A further process for separating NMEDA from EDA and water is disclosed in EP2507202. This disclosure teaches that the removal of NMEDA is effected in a rectification column at a column top pressure in the range from 0.01 bar to 4 bar and that the mixture to be distilled comprises at least a sufficient amount of water that the condition $H=a*X/Y$ is fulfilled, where H is the proportion by weight of water in the mixture to be distilled, X is the proportion by weight of water and Y is the proportion by weight of EDA at the azeotropic point of a binary mixture of water and EDA at the column pressure in question, and a is a real number having a value of 0.9 or more.

In a recent disclosure (WO 2019/081284), a process for the separation of NMEDA from EDA and water is disclosed where the NMEDA-separation column is operated at a bottom temperature of 155° C. and less and where the NMEDA-separation column comprises 50 to 140 theoretical plates. NMEDA is drawn-off at the top of the column and the azeotropic mixture of EDA/water is drawn-off at the bottom of the column.

After the removal of NMEDA, the EDA/water mixture is separated.

DE 1258413 discloses the separation of EDA and water in a single dewatering column which is operated at pressures where the azeotrope between water and EDA is broken, so that water can be drawn-off at the top of the distillation column and EDA and other amines are drawn-off from the sump.

Alternatively, EDA and water may be separated in two columns operated at different pressures (dual pressure distillation or pressure swing distillation) (see Fulgueras, A. M., Poudel, J., Kim, D. S. et al. Korean J. Chem. Eng. (2016) 33: 46. https://doi.org/10.1007/s11814-015-0100-4).

It was an object of the present invention to provide a process for purifying a mixture of EDA, NMEDA and water so as to achieve an on-spec EDA having a low NMEDA content, preferably an NMEDA content of 1000 ppm by weight or less. A further object of the invention was to reduce the number of columns required for the separation of the three components and/or the size of the equipment required, in order to reduce investment costs.

The object of the present invention was achieved by a a process for producing EDA from a mixture comprising water (H2O), ethylenediamine (EDA) and N-methylethylenediamine (NMEDA) by feeding the mixture into a rectification column, wherein the rectification column is operated at the top pressure in the range of 5.0 to 7.5 bar. It has been surprising found, that NMEDA and water can be efficiently separated from EDA in a single rectification column, if the rectification column is operated in a narrow pressure range. Accordingly, the number of rectification columns necessary to obtain EDA meeting the quality specifications demanded The following abbreviations are used hereinafter:
AEEA: aminoethylethanolamine
AEP: aminoethylpiperazine
DETA: diethylenetriamine
EDA: ethylenediamine
EDC: ethylene dichloride
HEP: hydroxyethylpiperazine
HPA: heavy polyamines
MEA: monoethanolamine
MEG: monoethylene glycol
NMEDA: N-methylethylenediamine
PEHA: pentaethylenehexamines
PIP: piperazine
TEPA: tetraethylenepentamine
TETA: triethylenetetramine Unless specified otherwise, pressure figures relate to the absolute pressure figure.

Mixtures

According to the invention, EDA is produced from mixtures comprising NMEDA, EDA and water.

Preparation of the Mixtures

Such mixtures can be prepared by first conducting an EDA preparation process. After the EDA preparation process, ammonia and hydrogen are generally removed.

In the preferred embodiment, the EDA-mixtures obtained after ammonia and/or hydrogen removal are used directly in the process of the invention without further workup steps.

In a further embodiment, the EDA-mixtures obtained after ammonia and/or hydrogen removal are subjected to a complete or partial removal of the higher-boiling amines (removal of the higher-boiling amines).

EDA Preparation Process

The first stage for preparation of the mixtures which can be used in the process of the invention is typically an EDA preparation process.

EDA can be prepared by various processes.

In a preferred embodiment (MEA process), EDA is prepared by reaction of MEA with NH3.

In a further preferred embodiment (C1 process), EDA is prepared by reaction of formaldehyde, hydrogen cyanide, ammonia and hydrogen.

In a further preferred embodiment (EDC process), EDA is prepared by reaction of ethylene dichloride with ammonia (EDC process).

In yet a further preferred embodiment (MEG process), EDA can be prepared by reaction of MEG with ammonia.

MEA Process

The reaction of MEA and ammonia is described, for example, in U.S. Pat. No. 2,861,995, DE-A-1 172 268 and U.S. Pat. No. 3,112,318. An overview of the various process variants of the reaction of MEA with ammonia can be found, for example, in the PERP Report No. 138 "Alkyl-Amines", SRI International, March 1981 (especially pages 81-99, 117).

The reaction of monoethanolamine with ammonia is preferably conducted in a fixed bed reactor over a transition metal catalyst at 150-250 bar and 160-210° C. or over a zeolite catalyst at 1-20 bar and 280-380° C.

Transition metal catalysts used with preference comprise Ni, Co, Cu, Ru, Re, Rh, Pd or Pt or a mixture of two or more of these metals on an oxidic support (e.g. $Al_2O_3$, $TiO_2$, $ZrO_2$, $SiO_2$). Preferred zeolite catalysts are mordenites, faujasites and chabazites.

To achieve a maximum EDA selectivity, in the case of transition metal catalysis, a molar ratio of ammonia to monoethanolamine of 6-20, preferably 8-15, is generally employed, and, in the case of zeolite catalysis, generally 20-80, preferably 30-50.

The MEA conversion is generally kept between 10% and 80%, preferably 40-60%.

In continuous operation, preferably, a catalyst space velocity in the range of 0.3-0.6 kg/(kg*h) (kg MEA per kg cat. per hour) is established.

To maintain the catalyst activity, when metal catalysts are used, preference is given to additionally feeding 0.05-0.5% by weight (based on the $MEA+NH_3+H_2$ reaction input) of hydrogen into the reactor.

C1 Process

A reaction output can also be prepared by the reaction of formaldehyde, hydrogen cyanide, ammonia and hydrogen.

For instance, U.S. Pat. No. 2,519,803 describes a process for preparing ethylenediamine by the hydrogenation of a partly purified aqueous reaction mixture which results from an amination of formaldehyde cyanohydrin (FACH) and comprises aminoacetonitrile as intermediate. Formaldehyde cyanohydrin can in turn be obtained by reaction of formaldehyde with hydrogen cyanide. A process description for preparation of FACH can be found, for example, in application PCT/EP2008/052337, page 26, and in application WO-A1-2008/104582, page 30 (variants A) and B)), to which reference is made explicitly here.

DE-A 1 154 121 relates to a further process for preparing ethylenediamine, wherein the hydrogen cyanide, formaldehyde, ammonia and hydrogen reactants are reacted in the presence of a catalyst in a "one-pot" process.

WO-A1-2008/104592 relates to a process for preparing EDA by hydrogenation of aminoacetonitrile. Aminoacetonitrile is typically obtained by reaction of formaldehyde cyanohydrin with ammonia, where formaldehyde cyanohydrin is in turn generally prepared from hydrogen cyanide and ammonia.

Preferably, a reaction output comprising EDA and NMEDA is prepared by the process described in WO-A-2008/104592, to which reference is hereby explicitly made.

EDC Process

EDA can also be prepared by reaction of ethylene dichloride with ammonia (EDC process). The reaction of EDC with ammonia is described, for example, in EP 2346809, in the abovementioned PERP Report and in the references cited therein.

MEG Process

In a further embodiment, EDA can be prepared by reaction of MEG with ammonia. The reaction of MEG with ammonia can be effected in the liquid phase or the gas phase. Gas phase reactions are disclosed, for example, in CN 102190588 and CN 102233272, while reactions in the liquid phase are disclosed, for example, in U.S. Pat. Nos. 4,111,840, 3,137,730, DE 1 72 268 and WO 2007/093514.

Composition of the Reaction Outputs from the EDA Preparation Processes

The mixtures that are prepared by the abovementioned preparation processes comprise EDA, NMEDA and water.

Depending on the preparation method, the mixtures generally also comprise:
hydrogen;
ammonia;
higher-boiling amines;
ethylene glycol (MEG); and
organic by-products.

Higher-boiling amines refer hereinafter to acyclic and cyclic compounds that comprise 2 or more amine groups (primary, secondary or tertiary) or that comprise one or more amine groups and one or more OH groups, and that have a higher boiling point than EDA at the same pressure. Examples for higher-boiling amines are piperazine (PIP), monoethanolamine (MEA), diethylenetriamine (DETA), aminoethylethanolamine (AEEA), triethylenetetramine (TETA) and higher ethyleneamines (higher ethyleneamines refer hereinafter to those higher-boiling ethyleneamines having a higher boiling point than TETA, e.g TEPA).

Organic by-products refer hereinafter to all unconverted starting materials and reaction products that are not higher-boiling amines, MEG, water, hydrogen, ammonia or NMEDA.

Ammonia Removal

The mixtures from the abovementioned preparation processes generally comprise ammonia.

The amount of ammonia in the reaction outputs is typically in the range from 50% to 90% by weight, more preferably in the range from 60% to 85% by weight and most preferably in the range from 70% to 80% by weight.

Before the reaction outputs are used in the process of the invention, ammonia and/or hydrogen are preferably separated from the mixtures obtained by the abovementioned preparation processes.

Hydrogen and ammonia can be separated from the reaction mixture by methods known to those skilled in the art.

Preferably, the removal of ammonia and hydrogen is conducted by distillation or rectification.

This can be effected in distillation stills or rectification columns.

In the case of rectification, it is possible to use columns having a rectifying section and stripping section.

If the depletion of secondary components such as methylamine from the ammonia is required, the use of a rectifying section is advantageous.

Preference is given to using columns without a rectifying section since no reflux is required in that case, which reduces the energy demand of rectification.

The removal of hydrogen and ammonia can be conducted in a single stage at a particular pressure or in a staged manner in a series of setups in which the pressure is varied in order to match bottom and top temperatures such that they are practicable.

Preferably, the pressure and composition at the top and bottom are chosen such that the condensation temperature is higher than 20° C., more preferably higher than 30° C., most preferably higher than 35° C. If the condensation temperature is within the ranges mentioned, the condenser can be cooled with cooling water which is generally at a temperature of 20-80° C., preferably 30 to 70° C. and more preferably 35-50° C.

The bottom temperature is preferably 275° C. or less, more preferably 260° C. or less, most preferably 250° C. or less. The bottom temperature is preferably in a range of 200 to 275° C., more preferably in a range of 210 to 260° C. and most preferably in a range of 220 to 250° C.

While the setting of the pressure is crucial for the setting of the temperatures, the temperatures in the distillation are also affected by setting of a particular concentration. For instance, it is possible to increase the condensation temperature at the top by drawing off not only ammonia but also other components having a higher boiling point than ammonia, for example water, overhead as well. In this case, it is advantageous to operate the condenser in backmixed mode (called "closed condensation" by the person skilled in the art), such that the condensation takes place within a narrow temperature range. A suitable condenser for this type of condensation is one in which the condensation takes place in cocurrent with the outflow of the condensate, or a direct condenser in which cold liquid which is pumped in circulation is brought into contact with the vapors to be condensed.

Preferably, in a first stage, the majority of ammonia is distilled off at high pressure, for example higher than 10 bar, preferably higher than 15 bar, more preferably higher than 20 bar, while still permitting a particular ammonia concentration in the bottom, with which the desired bottom temperature is established. The hydrogen present in the reaction output is likewise removed overhead. Preferably, in a first condenser, the majority of the ammonia is condensed out of the vapors at a relatively high temperature. Hydrogen is enriched here in the gas phase in accordance with the dew point curve of the mixture. Since complete condensation of the mixture is not possible at standard ambient temperatures, this gives rise to a gaseous output in the condenser. The latter can preferably be introduced into a second condenser in which the temperature can be lowered further by cooling with a colder coolant, such that ammonia is further depleted from the gas phase and a second offgas with lower ammonia content is formed. The offgas from the first or second condenser can also be treated by scrubbing in order to recover the majority of the ammonia present therein. This can be effected by use of standard methods known to those skilled in the art, such as scrubbing columns or Venturi scrubbers. This involves contacting the offgas with a preferably cooled liquid having a higher boiling point than ammonia, preferably water. In a particularly preferred variant, the scrubbing water is taken from another stage in the same process. This affords an ammonia-enriched liquid stream and an ammonia-depleted off-gas which generally comprises hydrogen removed. This offgas can be sent to incineration or recycled into an EDA production process. More preferably, the ammonia-enriched stream is recycled into the ammonia removal, for example the stage into which the reaction output is introduced.

Further preferably, the ammonia-containing bottoms output from the first stage of the ammonia removal is guided into a second stage which is operated at a lower pressure than the first stage. The pressure in the second stage is adjusted such that the desired bottom temperature is established, with ammonia being present only in a low concentration, if at all, in the bottoms output from the second stage. The condensation temperature at the top of the second stage is adjusted by entrainment of a component having a higher boiling point than ammonia, preferably water, such that the resulting mixture can be condensed with the desired coolant, for example river water or ambient air. In a particularly preferred variant, the ammonia-comprising mixture drawn off overhead is recycled into the first stage.

It is also possible to subdivide the hydrogen and ammonia removal into a further (zeroth) stage which precedes the first stage and is operated at the same pressure but at a lower bottom temperature than the first stage, such that some of the ammonia can be evaporated at a lower temperature. In this way, cheaper energy at lower temperature, for example waste heat, can be used to save on energy costs. Preferably, the vapors from the zeroth stage are condensed in the same condenser as the vapors from the first stage.

Composition of the Output from the Ammonia Removal

After the removal of ammonia and optionally hydrogen, a mixture comprising not only water, EDA and NMEDA but generally also higher-boiling amines and organic by-products is obtained.

After the removal of NH3 and optionally hydrogen, the output from the hydrogen/ammonia removal can be used directly in the process of the invention.

The mixture obtained after the removal of ammonia, which can be used in the process of the invention, comprises preferably 20% to 75% by weight of EDA, more preferably 30% to 65% by weight of EDA and most preferably 35% to 60% by weight of EDA. The weight ratio of EDA to NMEDA is preferably
- 1:0.0005 (500 ppm by weight of NMEDA) to 1:0.2 (200 000 ppm by weight of NMEDA), more preferably 1:0.001 (1000 ppm by weight) to 1:0.05 (50 000 ppm by weight of NMEDA) and most preferably 1:0.005 (5000 ppm by weight of NMEDA) to 1:0.01 (10 000 ppm by weight of NMEDA).

The proportion of ammonia is preferably less than 5% by weight of ammonia, more preferably less than 2% by weight of ammonia, more preferably less than 1% by weight of ammonia and especially preferably less than 0.5% by weight.

The proportion of higher-boiling amines and other high boilers such as MEG is preferably in the range from 5% to 90% by weight, more preferably in the range from 30% to 85% by weight and most preferably in the range from 40% to 70% by weight.

In a preferred embodiment, the weight ratio of the above-mentioned components in the mixture used in the process is preferably:
- EDA:NMEDA=1:0.0005 to 0.2;
- EDA:ammonia=1:0 to 0.05;
- EDA:higher-boiling amines=1:0 to 2.0; and
- EDA:organic by-products=1:0 to 0.05;

and more preferably:
- EDA:NMEDA=1:0.001 to 0.05;
- EDA:ammonia=1:0 to 0.025;
- EDA:higher-boiling amines=1:0.05 to 1; and
- EDA:organic by-products=1:0.0001 to 0.025; and most preferably
- EDA:NMEDA=1:0.005 to 0.01;
- EDA:ammonia=1:0 to 0.025;
- EDA:higher-boiling amines=1:0.05 to 1; and
- EDA:organic by-products=1:0.0001 to 0.025.

In a further preferred embodiment, EDA is prepared by reaction of MEG and NH3. In this further particularly preferred embodiment, the weight ratio of the abovementioned components in the mixture used in the process is preferably:
- EDA:NMEDA=1:0.0005 to 0.2;
- EDA:ammonia=1:0 to 0.05;
- EDA:higher-boiling amines=1:0 to 2.0; and
- EDA:MEG=1:0.5 to 10.0
- EDA:organic by-products=1:0 to 0.05;

and more preferably:
- EDA:NMEDA=1:0.001 to 0.05;
- EDA:ammonia=1:0 to 0.025;
- EDA:higher-boiling amines=1:0.05 to 1; and
- EDA:MEG=1:1.0 to 8.0
- EDA:organic by-products=1:0.0001 to 0.025; and most preferably
- EDA:NMEDA=1:0.005 to 0.01;
- EDA:ammonia=1:0 to 0.025;
- EDA:higher-boiling amines=1:0.05 to 1; and
- EDA:MEG=1:2.0 to 5.0
- EDA:organic by-products=1:0.0001 to 0.025.

The mixtures obtained after the removal of ammonia can be used directly in the process of the invention.

Removal of the Higher-Boiling Amines

As an alternative to the direct use of the mixture after the removal of ammonia, it is possible to partially or completely remove the higher-boiling amines and other high boilers, for example MEG.

In a preferred embodiment, after the removal of ammonia, all higher-boiling amines (including PIP) are removed.

This is preferably effected in a rectification column which is operated in such a way that the higher-boiling amines are obtained in the lower part of the column, preferably in the bottom of the column, and a mixture comprising water, NMEDA and EDA is drawn off in the upper region of the columns, preferably at the top of the column.

The exact operating conditions of the rectification column can, in accordance with the separation performance of the column used, be determined in a routine manner by the person skilled in the art by customary calculation methods using the known vapor pressures and evaporation equilibria of the components introduced into the rectification column.

At the top of the column, a mixture that can be used in the process of the invention for removal of NMEDA and EDA is obtained.

In a further embodiment, all higher-boiling amines and other high boilers, for example MEG, apart from PIP are removed.

This is preferably effected in a rectification column which is operated in such a way that the higher-boiling amines apart from PIP are obtained in the lower part of the column, preferably in the bottom of the column, and a mixture comprising water, NMEDA, EDA and PIP is drawn off in the upper region of the columns, preferably at the top of the column.

The exact operating conditions of the rectification column can, in accordance with the separation performance of the column used, be determined in a routine manner by the person skilled in the art by customary calculation methods using the known vapor pressures and evaporation equilibria of the components introduced into the rectification column.

At the top of the column, a mixture that can be used in the process of the invention for removal of NMEDA and EDA is obtained.

Composition of the Mixtures After Removal of the Higher-Boiling Amines

In an embodiment in which the higher-boiling amines and other high boilers, for example MEG, are partially or completely removed, the weight ratio of the abovementioned components in the mixture used in the process is preferably:
- EDA:NMEDA=1:0.0005 to 0.2;
- EDA:ammonia=1:0 to 0.05;
- EDA:PIP=1:0 to 0.05
- EDA:higher-boiling amines=1:0 to 0.1 and
- EDA:MEG=1:0 to 0.1
- EDA:organic by-products=1:0 to 0.05;

and more preferably:
- EDA:NMEDA=1:0.001 to 0.05;
- EDA:PIP=1:0 to 0.02;
- EDA:ammonia=1:0 to 0.025;
- EDA:higher-boiling amines=1:0 to 0.05; and
- EDA:MEG=1:0 to 0.05
- EDA:organic by-products=1:0.0001 to 0.025; and most preferably
- EDA:NMEDA=1:0.005 to 0.01;
- EDA:ammonia=1:0 to 0.025;
- EDA:PIP=1:0 to 0.01

EDA:higher-boiling amines=1:0 to 0.02; and
EDA:MEG=1:0 to 0.001
EDA:organic by-products=1:0.0001 to 0.025.

In an embodiment in which the higher-boiling amines and other high boilers, for example MEG, apart from PIP are partially or completely removed, the weight ratio of the abovementioned components in the mixture used in the process is preferably:
EDA:NMEDA=1:0.0005 to 0.2;
EDA:ammonia=1:0 to 0.05;
EDA:PIP=1:0.1 to 2
EDA:higher-boiling amines=1:0 to 0.1 and
EDA:MEG=1:0 to 0.1
EDA:organic by-products=1:0 to 0.05;
and more preferably:
EDA:NMEDA=1:0.001 to 0.05;
EDA:PIP=1:0.2 to 1;
EDA:ammonia=1:0 to 0.025;
EDA:higher-boiling amines=1:0 to 0.05; and
EDA:MEG=1:0 to 0.05
EDA:organic by-products=1:0.0001 to 0.025; and
most preferably
EDA:NMEDA=1:0.005 to 0.01;
EDA:ammonia=1:0 to 0.025;
EDA:PIP=1:0.3 to 0.5
EDA:higher-boiling amines=1:0 to 0.02; and
EDA:MEG=1:0 to 0.001
EDA:organic by-products=1:0.0001 to 0.025.

Amount of Water:

The mixtures fed into the inventive process also comprise water. The content of water in the mixtures comprising EDA, NMEA and water is preferably in the range of 10 to 80 percent by weight, more preferably in the range of 15 to 70 percent by weight, even more preferably in the range of 20 to 50 percent by weight and most preferably in the range of 25 to 50 percent by weight.

EDA-Dewatering;

The mixtures comprising EDA, NMEDA and water are fed into a rectification column (EDA-de-watering column).

In the EDA-dewatering column, a separation is generally effected into a low-boiling fraction comprising water and the major portion of NMEDA, and a high-boiling fraction comprising the major proportion of EDA and any higher-boiling amines and any MEG if these have not already been partly or completely removed from the mixture beforehand.

The rectification can be effected in rectification apparatuses, such as tray columns, such as bubble-cap tray columns, sieve tray columns, dual flow tray columns, valve tray columns, baffle tray columns or columns having random packings or structured packings. Preference is given to using internals with a low pressure drop, such as structured packings, for example in the form of sheet metal packing such as Mellapak 250 Y or Montz Pak (B1-250 type). It is also possible for a packing with lower or elevated specific surface area to be present, or it is possible to use a fabric packing or a packing with another geometry such as Mellapak 252.Y. The advantages for the use of such internals are the low pressure drop and low specific liquid holdup compared to valve trays, for example. The internals may be disposed in one or more beds.

In a preferred embodiment the rectification according to the invention is conducted in a column equipped with trays (tray column). It has been found that tray columns provide an improved efficiency compared to packed columns for aqueous EDA-mixtures. Most preferably the column is a bubble-cap tray column, a sieve tray column, a dual flow tray column, a valve tray column or a baffle tray column. Most preferably, the column is a is a bubble-cap tray column or a sieve tray column.

According to the process of the invention, the pressure in the EDA-dewatering column is in the range of 5.0 to 7.5 bar, preferably in the range of 5.1 to 7.0 bar, more preferably in the range of 5.2 to 6.5 bar, even more preferably in the range of 5.3 to 6.3 and most preferably in the range of 5.5 to 6.0 bar.

In a preferred embodiment, the EDA-dewatering column is operated at top pressure at which EDA and water form a zeotrope or zeotropic mixture, in which EDA and water have different boiling points and can be separated by distillation.

Surprisingly it has been found, that when the rectification is conducted in the inventive pressure range, most of the NMEDA is separated off with the water as the lower boiling fraction. It has also been found, that EDA losses at the top of the column can be reduced, if the pressure is within the claimed and preferred ranges.

The number of theoretical plates in the EDA-dewatering column is generally in the range from 20 to 120, preferably 30 to 110 more preferably 35 to 100.

In a preferred embodiment, the number of theoretical plates is in the range of 40 to 90. If the number of theoretical plates is sufficiently high, the EDA losses in the fraction drawn-off at the top of the column can be further reduced. At pressures slightly above the pressures where an azeotrope between EDA and water is formed, the difference in vapor pressure or boiling points between water and EDA may still be low, so that an improved separation may be obtained using columns having a number of theoretical plates within the afore-mentioned ranges.

The energy required for the evaporation of the mixture comprising EDA, NMEDA and water in the EDA-dewatering column is typically introduced by an evaporator in the bottom of the column. This evaporator is typically a natural circulation evaporator or forced circulation evaporator. Alternatively, it is possible to use evaporators with a short residence time, such as falling-film evaporators, helical tube evaporators, wiped-film evaporators or a short-path evaporator.

The feed comprising EDA, NMEDA and water is preferably introduced in a spatial region between 50% and 100% of the theoretical plates of the EDA-dewatering column. For example, the feed may be to the top of the column. Preferably, the feed is preferably introduced between 60 to 80% of the theoretical plates and more preferably between 65 to 80% of the theoretical plates. For examples, if the column has 50 theoretical plates, the feed is preferably introduced between plate 33 and 40 (65 to 80%).

In a preferred embodiment, the EDA-dewatering column has a condenser which is generally operated at a temperature at which the predominant portion of the water is condensed at the corresponding top pressure.

In general, the operating temperature of the condenser is in the range from 150 to 230° C., preferably 160 to 195° C.

Condensers used may, for example, be condensers having cooling coils or helical tubes, jacketed tube condensers and shell and tube heat exchangers.

A condensate comprising predominantly water and NMEDA is generally obtained in the condenser.

Preferably, the condensate comprises 98 wt.-% or more of water, preferably 99 wt.-% or more of water and more preferably 99.5 wt.-% or more of water.

Preferably, the condensate comprises 2 wt.-% or less of EDA, preferably 1 wt.-% or less of EDA and more preferably 0.5 wt.-% or less of EDA.

Preferably, the condensate obtained in the condenser is preferably recycled into the top of the EDA-dewatering column to an extent of 50 vol.-% or more, preferably to an extent of more than 65% vol.-%, or more, more preferably to an extent of 70 vol. % or more, based on the total condensate volume.

In a preferred embodiment, the reflux ratio, which is the ratio of condensate flow returned to the column to the condensate flow removed from the process, is preferably in the range of 1:1 to 5.0:1, more preferably in the range of 1.25:1 to 4.75:1, even more preferably in the range of 1.5:1 to 4.5:1, still more preferable in the range of 1.75:1 to 4,25;1 and most preferably in the range of 2.0:1 to 4.0:1. In this embodiment, the losses of EDA at the top of the EDA-dewatering column can be reduced while reducing the concentration of NMEDA at the bottom of the EDA-dewatering column without sacrificing the energy consumption of the column (reboiler duty) or the column-throughput.

The unrecycled condensate can be sent directly to disposal, for example by introduction into a wastewater treatment plant.

More preferably, the unrecycled condensate from the EDA-dewatering column is fed to a waste water treatment column, wherein residual organic components, such as the NMEDA, are separated from the water.

The waste water treatment column is preferably operated between 0.5 to 2 bar, more preferably 0.75 to 1.5 and even more preferably 0.9 to 1.1 bar. In the most preferable embodiment, the waste water treatment column is operated at atmospheric pressure.

The energy required for the evaporation of the mixture comprising NMEDA and water in the waste water treatment column is typically introduced by an evaporator in the bottom of the column. This evaporator is typically a natural circulation evaporator or forced circulation evaporator. Alternatively, it is possible to use evaporators with a short residence time, such as falling-film evaporators, helical tube evaporators, wiped-film evaporators or a short-path evaporator. The number of theoretical plates of the waste water treatment column is generally in the range from 5 to 50, preferably 10 to 40, more preferably 15 to 30 and most preferably 18 to 25.

The feed comprising NMEDA and water to the waste water treatment column is preferably introduced in a spatial region between 40% and 60% of the theoretical plates of the rectification column.

In a preferred embodiment, the waste water treatment column has a condenser which is generally operated at a temperature at which the predominant portion of the water is condensed at the corresponding top pressure. In general, the operating temperature of the condenser is in the range from 15 to 50° C. and preferably 20 to 40° C.

Condensers used may, for example, be condensers having cooling coils or helical tubes, jacketed tube condensers and shell and tube heat exchangers.

A condensate comprising predominantly water is generally obtained in the condenser.

Preferably, the condensate obtained in the condenser is preferably recycled into the top of the waste water treatment column to an extent of 50 vol.-% or more, preferably to an extent of more than 65% vol.-% or more and more preferably to an extent of 70 vol. % or more, based on the total condensate volume.

The high boiling output from the waste water treatment column obtained at the bottom of the waste water treatment column comprises essentially amines, such as NMEDA and water. The sump product, comprising water and NMEDA is preferably send to burner for incineration.

The high-boiling output from the EDA-dewatering column comprises essentially EDA and any higher-boiling amines and any MEG.

Preferably, the high-boiling output from the EDA-dewatering column comprises less than 1.0% by weight of water, preferably less than 0.6% by weight and more preferably less than 0.5% by weight of water.

Preferably, the high-boiling output from the EDA-dewatering column comprises less than 0.5% by weight of NMEDA, more preferably less than 0.3% by weight of NMEDA and most preferably less than 0.1% by weight of NMEDA.

This output can, as described below, be separated into its individual components or suitable fractions in order to obtain, for example, on-spec EDA.

EDA-PIP Removal

When the high-boiling output from the EDA dewatering column comprises both EDA and higher-boiling amines, with or without MEG, there is generally first a separation into a lower-boiling fraction comprising PIP and EDA, and a higher-boiling fraction generally comprising the higher-boiling amines than PIP and any MEG. This separation can likewise be conducted in the rectification column (EDA-PIP removal). The exact operating conditions of the rectification column can, in accordance with the separation performance of the column used, be determined in a routine manner by the person skilled in the art by customary calculation methods using the known vapor pressures and evaporation equilibria of the components introduced into the rectification column. For example, the EDA-PIP removal can be conducted as described in EP 2 507 202 or in the aforementioned PRP Report, page 89 et seq. in conjunction with FIG. 6.1, to which reference is hereby made explicitly.

The higher-boiling fraction is preferably drawn on at the bottom of the rectification column and generally comprises the higher-boiling amines.

The higher-boiling amines can be separated into the pure substances or suitable fractions by means of customary methods, especially by rectification. The workup of the higher-boiling amines is likewise described in the aforementioned PRP Report, page 89 et seq. in conjunction with FIG. 6.1 or EP 2487151, EP2507202 or EP2346809.

The lower-boiling fraction which is preferably drawn off in the upper region of the columns typically comprises EDA and PIP and is generally predominantly free of other higher-boiling amines. The proportion of higher-boiling amines (excluding piperazine) is generally less than 0.2% by weight, preferably less than 0.1% by weight and more preferably less than 0.05% by weight. In order to obtain on-spec EDA, the low-boiling EDA-PIP fraction is generally sent to a further purification stage (purifying EDA distillation).

Purifying EDA Distillation

The low-boiling fraction from the EDA/PIP removal is typically introduced into a further rectification column (purifying EDA distillation) which is preferably operated in such a way that EDA is obtained at the top of the column and piperazine can be drawn off at the bottom of the column. The exact operating conditions of the rectification column can, in accordance with the separation performance of the column used, be determined in a routine manner by the person skilled in the art by customary calculation methods using the known vapor pressures and evaporation equilibria of the components introduced into the rectification column. For example, the EDA-PIP removal can be conducted as described in EP 2 507 202 or in the aforementioned PRP Report, page 89 et seq. and FIG. 6.1, to which reference is hereby made explicitly.

In the condenser, a condensate comprising predominantly EDA but only very small amounts of NMEDA is generally obtained.

The low-boiling EDA-comprising fraction thus obtained is generally predominantly free of higher-boiling amines, including piperazine. The proportion of higher-boiling amines, including piperazine, is generally less than 0.5% by weight, preferably less than 0.3% by weight and more preferably less than 0.2% by weight.

In addition, the low-boiling EDA-comprising fraction preferably comprises 99.5% by weight or more of EDA.

The concentration of NMEDA in the EDA-containing fraction is preferably in the range from 0.001% to 0.1% by weight, preferably 0.005% to 0.08% by weight and more preferably in the range from 0.01% to 0.05% by weight.

Preferred Combinations

The above-detailed process steps and the respective embodiments of the individual process steps can be combined with one another in a suitable manner, and so the present invention also encompasses suitable combinations of the above-detailed process steps and the respective embodiments.

More particularly, the following combinations are preferred:

Combination of an EDA preparation process which is an EDA process with an ammonia removal, a rectification according to the invention, an EDA-PIP removal and a purifying EDA distillation.

Combination of an EDA preparation process which is a MEG process with an ammonia removal, a rectification according to the invention, an EDA-PIP removal and a purifying EDA distillation.

Combination of an EDA preparation process which is a C1 process with an ammonia removal, a rectification according to the invention, an EDA-PIP removal and a purifying EDA distillation.

Combination of an EDA preparation process which is an EDC process with an ammonia removal, a rectification according to the invention, an EDA-PIP removal and a purifying EDA distillation.

Advantages and Applications

EDA which has been obtained after the purifying EDA distillation is advantageously suitable for applications where very high purity of the EDA is important.

The EDA thus obtained can be used, for example, for preparation of high molecular weight polymers such as polyamides, since the functionality of the EDA is not reduced by the formation of NMEDA. For example, the EDA thus obtained can also be used as an electronics chemical or as a high-purity chemical for use in the field of crop protection agents, pesticides, epoxy resins, complexing agents, or for applications in the leather industry (leather chemicals), the paper industry (paper chemicals), the automotive and fuel industry (fuel additives, gasoline additives, lubricants), the textile industry (textile resins and polymers) or the detergents industry (detergents, bleach additives). The use of high-purity chemicals increases the yield of end product, reduces the concentration of unwanted by-products and can also lead to an improvement in the use and processing properties in the fields of use in question. For instance, NMEDA, in polycondensation reactions, for example in the preparation of epoxy resins or polyamides, can lead to unwanted chain termination reactions which can reduce the degree of polymerization or the density at network points. Accordingly, the present application is also directed to a process, comprising the step of producing EDA according to the invention and further converting the EDA to polyamides, electronic chemicals, crop protection agents, pesticides, epoxy resins, complexing agents, leather chemicals, paper chemicals, textile resins, fuel and gasoline additives, lubricants, bleach additives or detergents.

By means of the process of the invention for removing NMEDA from a mixture comprising EDA, NMEDA and water which is obtained in the preparation of EDA, it is possible to obtain an onspec EDA having a content of at least 99.5% by weight of EDA and an NMEDA content of 1000 ppm by weight or less even when greater amounts of NMEDA form in the preparation of EDA. This may be the case, for example, when EDA is prepared from C1 units, such as formaldehyde and hydrogen cyanide, or when catalysts show partial activation with increasing operating time and the reaction temperature has to be increased to compensate for the deactivation. The increase in the temperature generally results in a deterioration in selectivity in relation to the preparation of EDA, and increased formation of NMEDA as by-product. Thus, the process of the invention also enables an increase in the periods of use of catalysts in the preparation of EDA.

By means of the process of the invention, it is also possible to obtain a high-purity EDA that can be used as starting material in a multitude of applications with increased yields and fewer side reactions.

The process of the invention additionally has the advantage that the separation and/or equipment complexity and energy expenditure in the rectification is reduced enabling the reduction of CAPEX and OPEX in EDA-production The process of the invention is elucidated by examples which follow.

EXAMPLE 1

The examples are bases on calculation performed on the basis of a thermodynamic model using the NRTL model for the description of the vapour-liquid equilibrium of water, EDA, NMEDA and other higher boiling amines.

A feed of 17800 kg/h comprising 25 wt.-% water, 33 wt.-% EDA, 1400 wt.-ppm NMEDA, high boiling amines like DETA, AEEA, TETA and TEPA was fed on the $34^{th}$ theoretical plate of a column with a total of 47 theoretical plates. The pressure at the top of the column was varied from 4.6 to 8.8 bar.

Figure 1:
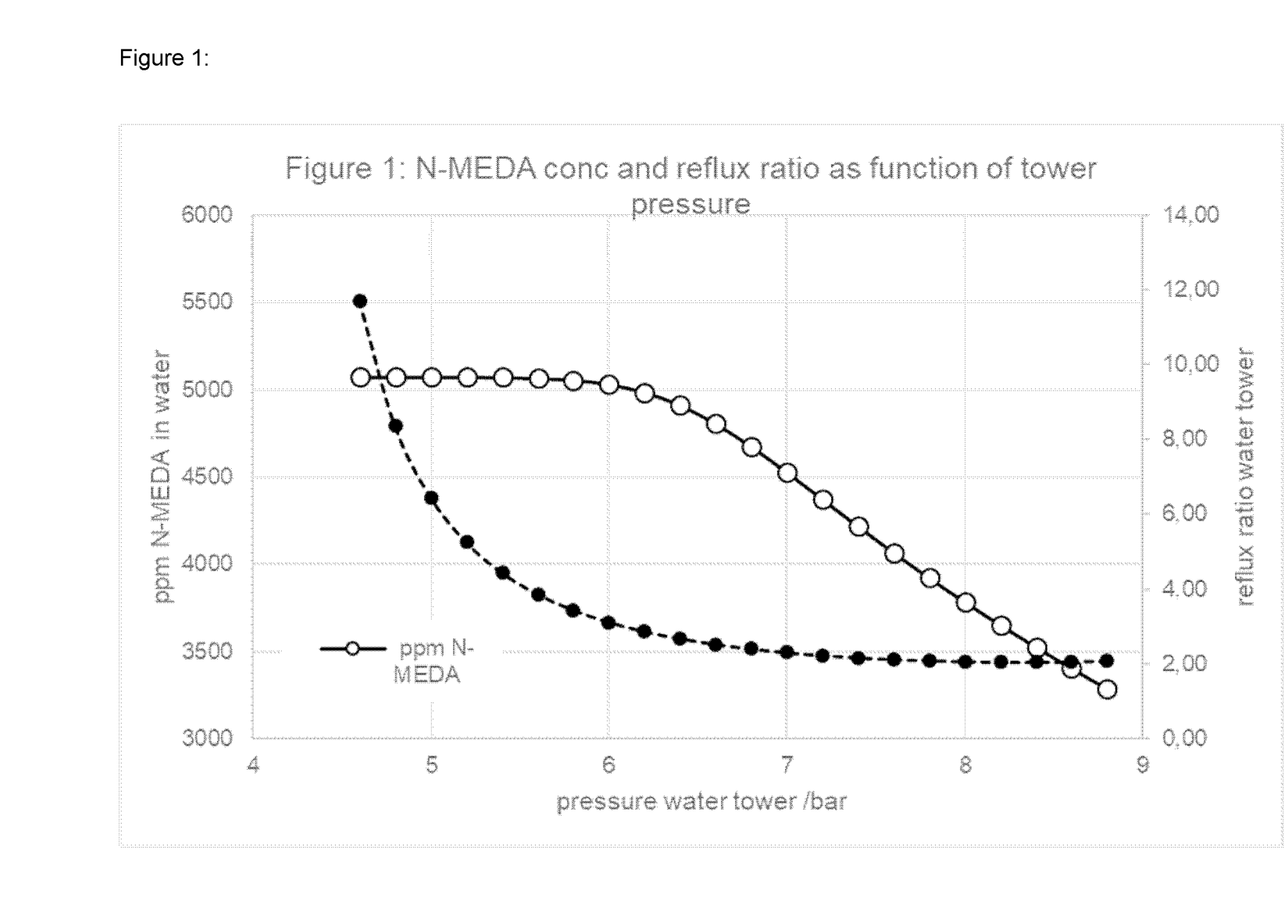
FIG. 1 shows the concentration of NMEDA as function of the tower pressure in the tip of the water separation tower.

The concentration of NMEDA as function of the tower pressure in the top of the water separation tower is depicted in FIG. 1. With decreasing top pressure, the concentration of NMEDA in the process water is increasing until nearly all NMEDA is separated from the other amines. FIG. 1 also shows the reflux ration required to maintain an EDA concentration of less than 100 ppm in the distillate removed at the top of the distillation tower. With decreasing pressure, the separation is becoming more difficult expressed by the increasing reflux ratio of the tower.

Figure 2:
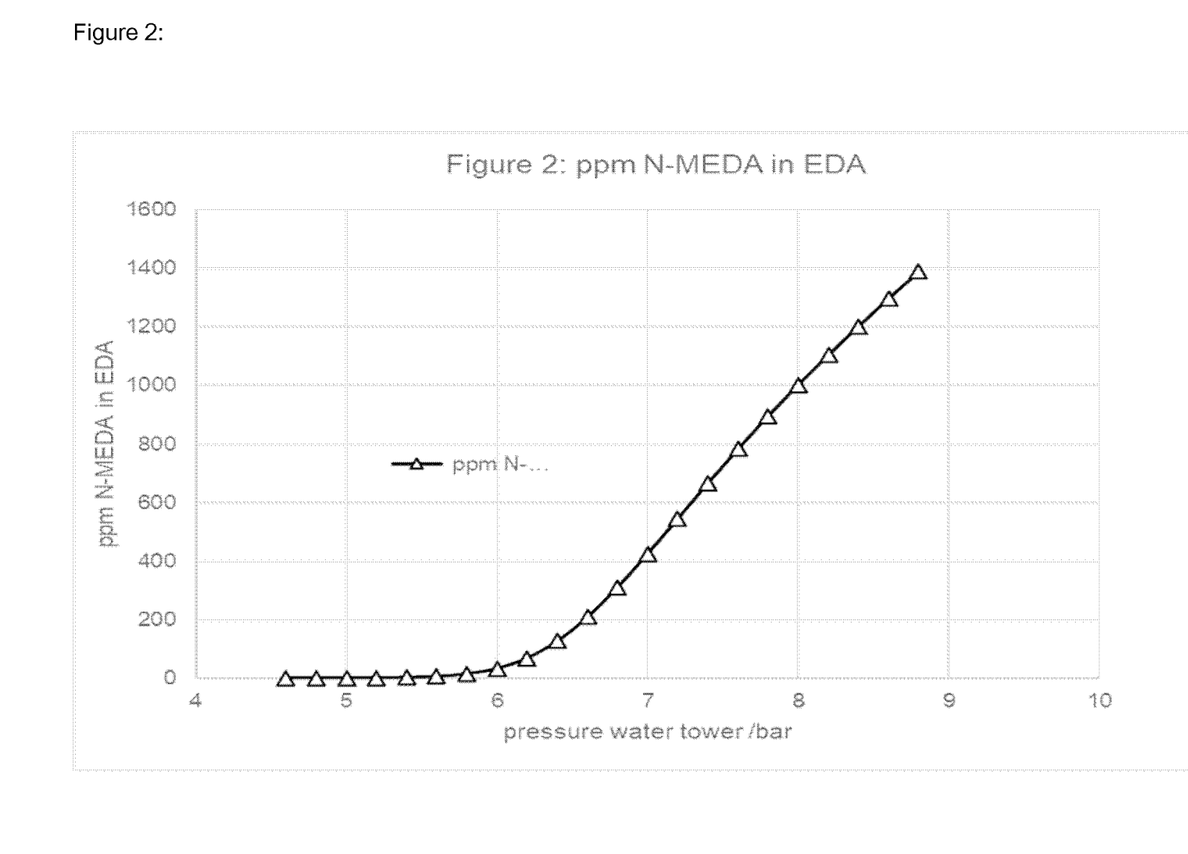
FIG. 2 shows the NMEDA concentration in the product EDA as function of the top pressure of the EDA-water separation.

FIG. 2 depicted the NMEDA concentration in the product EDA as function of the top pressure of the EDA-water separation. With decreasing pressure, the concentration of NMEDA in EDA is decreasing.

It can be seen, that above a pressure of 7.0 bar, the NMEDA concentration rises to values which make it difficult to obtain the EDA specifications demanded in the market. Under the pressure of 5.0 bar it's difficult to separate EDA from process water. Surprisingly, the separation is best affected at a top pressure in the narrow range of 5.0 to 7.5 bar.

The invention claimed is:

1. A process for producing ethylenediamine (EDA) from a mixture comprising water (H2O), EDA and N-methylethylenediamine (NMEDA) by feeding the mixture into a rectification column, wherein the rectification column is operated at the top pressure in the range of 5.0 to 7.5 bar and the weight ratio EDA to NMEDA in the mixture comprising water (H2O), ethylenediamine (EDA) and N-methylethylenediamine (NMEDA) fed into the rectification column is 1:0.0005 to 1:0.2.

2. The process according to claim 1, wherein the pressure at the top of the rectification column is in the range of 5.1 to 7.0 bar.

3. The process according to claim 1, wherein the rectification column has 40 to 90 theoretical plates.

4. The process according to claim 1, wherein the reflux ratio in the column is in the range of 2:1 to 4:1.

5. The process according to claim 1, wherein the rectification is a tray column.

6. The process according to claim 1, wherein the mixture comprising water, EDA and NMEDA is introduced in a spatial region between 60 to 80% of the theoretical plates.

7. The process according to claim 1, wherein the mixture comprising EDA, water and NMEDA is obtained from an ethylenamine producing process.

8. The process according to claim 1, wherein the mixture comprising EDA, water and NMEDA is obtained by the reaction of monoethanolamine and ammonia.

9. The process according to claim 1, wherein a mixture comprising EDA and higher boiling amines is obtained as a higher boiling fraction at the bottom of the rectification column and wherein the higher boiling fraction is fed into a rectification column in which EDA and PIP are obtained as the lower boiling fraction and the higher boiling amines are obtained as the higher boiling fraction and wherein the mixture of EDA and PIP is fed to a rectification column in which EDA is obtained as the lower boiling fraction and PIP is obtained as the higher boiling fraction.

10. The process according to claim 1, wherein the rectification column is operated at a top pressure at which EDA and water form a zeotropic mixture.

11. The process according to claim 1, wherein a mixture of water and NMEDA is obtained as a lower boiling fraction at the top of the rectification column.

12. The process according to claim 11, wherein the mixture obtained at the top of the rectification column is fed to a waste water treatment column and is separated into a high boiling fraction comprising water and NMEDA and a low boiling fraction comprising water.

13. The process according to claim 1, wherein ammonia and/or hydrogen has been removed from the mixture comprising water (H2O), ethylenediamine (EDA) and N-methylethylenediamine (NMEDA) before feeding the mixture into the rectification column.

14. The process according to claim 1, further converting the EDA to polyamides, electronic chemicals, crop protection agents, pesticides, epoxy resins, complexing agents, leather chemicals, paper chemicals, textile resins, fuel and gasoline additives, lubricants, bleach additives or detergents.

15. The process according to claim 13, wherein the mixture obtained after the removal of ammonia comprises 20 to 75 percent by weight of EDA.

* * * * *